(12) United States Patent
Chiba

(10) Patent No.: US 7,198,255 B2
(45) Date of Patent: Apr. 3, 2007

(54) LIQUID BAG, LIQUID BAG MOUTH MEMBER, AND METHOD OF PRODUCING THE SAME

(75) Inventor: Mitsuru Chiba, Kanagawa (JP)

(73) Assignee: Senko Medical Instrument Mig. Co., Ltd., Tokyo (JP)

(*) Notice: Subject to any disclaimer, the term of this patent is extended or adjusted under 35 U.S.C. 154(b) by 0 days.

(21) Appl. No.: 10/521,460

(22) PCT Filed: Jul. 23, 2003

(86) PCT No.: PCT/JP03/09303

§ 371 (c)(1),
(2), (4) Date: Jan. 28, 2005

(87) PCT Pub. No.: WO2004/011073

PCT Pub. Date: Feb. 5, 2004

(65) Prior Publication Data

US 2006/0202362 A1    Sep. 14, 2006

(30) Foreign Application Priority Data

Jul. 25, 2002    (JP) .............................. 2002-216825

(51) Int. Cl.
*B01F 3/04* (2006.01)
(52) U.S. Cl. ............... 261/122.1; 261/124; 128/200.13
(58) Field of Classification Search ............. 261/121.1, 261/124, 122.1, DIG. 65; 128/200.11, 200.13
See application file for complete search history.

(56) References Cited

U.S. PATENT DOCUMENTS 3,807,713 A * 4/1974 Cornett et al. ........... 261/122.1
4,012,471 A * 3/1977 Kunkle, Jr. ................. 261/124
4,012,472 A   3/1977 Lindsey
4,025,590 A * 5/1977 Igich ....................... 261/122.1

(Continued)

FOREIGN PATENT DOCUMENTS

| EP | 0766955 | 4/1997 |
|----|---------|--------|
| JP | 62-24833 | 2/1987 |
| JP | 2-4671 | 1/1990 |

(Continued)

OTHER PUBLICATIONS

English Language Abstract of JP 2000-190997.

(Continued)

*Primary Examiner*—Scott Bushey
(74) *Attorney, Agent, or Firm*—Greenblum & Bernstein, P.L.C.

(57) ABSTRACT

An object of the present invention is to provide a liquid bag that makes bubbling possible with a simple structure without increasing the number of parts.

The liquid bag according to the present invention includes: a bag main body for containing a liquid, the bag main body constructed of a flexible thermoplastic resin sheet; and a mouth member constructed of a thermoplastic resin, the mouth member sealingly bonded to a part of a periphery of the bag main body. The mouth member has a sleeve-like seal portion sealingly bonded to the bag main body, the seal portion including a first flow path and a second flow path. The first flow path opens and extends along the periphery of the bag main body and the second flow path opens at a bottom surface of the seal portion to an inside of the bag main body.

5 Claims, 7 Drawing Sheets

U.S. PATENT DOCUMENTS

| | | | | |
|---|---|---|---|---|
| 4,036,919 | A | * | 7/1977 | Komendowski et al. .. 261/122.1 |
| 4,061,698 | A | * | 12/1977 | Thornwald ................ 261/78.2 |
| 4,138,970 | A | * | 2/1979 | Harmon .................... 123/25 R |
| 4,187,951 | A | * | 2/1980 | Cambio, Jr. .................... 215/6 |
| 4,367,182 | A | * | 1/1983 | Kienholz .................... 261/124 |
| 4,861,523 | A | * | 8/1989 | Beran ........................ 261/104 |
| 4,865,777 | A | * | 9/1989 | Weiler et al. ............ 261/122.1 |
| 6,773,426 | B2 | * | 8/2004 | Tamari ....................... 604/406 |

FOREIGN PATENT DOCUMENTS

| | | |
|---|---|---|
| JP | 2000-190997 | 7/2000 |
| WO | 98/48765 | 11/1998 |

OTHER PUBLICATIONS

English Language Abstract of JP 2-4671.

* cited by examiner

LIQUID BAG, LIQUID BAG MOUTH MEMBER, AND METHOD OF PRODUCING THE SAME

TECHNICAL FIELD

The present invention relates to a liquid bag, a mouth member for the liquid bag and a production method thereof, and more particularly, to a liquid bag usable as a device for adding moisture (water vapor or water in spray form) to a gas such as air, oxygen, nitrogen, carbon dioxide or the like, and especially as a humidifier or nebulizer (sprayer) for oxygen.

BACKGROUND ART

Among conventional liquid bags comprising a bag main body constructed of a flexible thermoplastic resin sheet, known are liquid bags 1, 2 and 3 mentioned below.
1. A liquid bag wherein a mouth member having one mouth portion is sealingly bonded to a part of the periphery of a bag main body shaped like an envelop.
2. A liquid bag wherein a mouth member having two mouth portions is sealingly bonded to a part of the periphery of a bag main body shaped like an envelop (For example, Japanese Unexamined Patent Publication No. 2000-190997).
3. A double-chamber liquid bag wherein a mouth member having one mouth portion is sealingly bonded to a part of the periphery of a bag main body shaped like an envelop and wherein parts of opposed sheets of the bag main body are heat-welded by a special heat-sealing method to partition an inside of the liquid bag into two chambers. This liquid bag is constructed so that applying a pressure onto one chamber penetrates the welded part partitioning the two chambers and thus liquid preparations contained in each of the chambers are mixed (For example, Japanese Unexamined Patent Publication No. Hei 2(1990)-4671).

Among unsophisticated oxygen inhalers (humidifiers) for supplying oxygen with moisture (water vapor or water in spray form) beforehand added thereto, known is an inhaler wherein an oxygen-introducing pipe is attached to a cylindrical hard bottle. For use of the inhaler, however, sterilized water needs to be introduced therein, which is a cumbersome and time-consuming operation and also poses sanitary problems. For the hard bottle, a disposable hard bottle shaped in a box is also usable. However, such a disposable hard bottle is bulky, which results in an upsize of the production apparatus, increasing the manufacturing costs. The hard bottle is also inconvenient in disposal. For these reasons, it is conceived to add a bubbling function to a liquid bag constructed of a flexible container. However, adding the bubbling function to the liquid bags 1, 2 and 3 makes it necessary to provide another member such as a tube or the like for introducing a gas into the bag main body. Especially for the liquid bags 1 and 3 wherein their ports have only one mouth portion, it is necessary to provide another port having a mouth portion for discharging air introduced in the bag main body to the outside, which results in an increase in the number of parts and the complexity in the manufacturing process, driving up costs.

A main object of the present invention is to provide a liquid bag that makes bubbling possible with a simple structure without increasing the number of parts, a mouth member for the liquid bag and a production method thereof.

DISCLOSURE OF INVENTION

The present invention provides a liquid bag which is characterized by providing: a bag main body for containing a liquid, the bag main body constructed of a flexible thermoplastic resin sheet; and a mouth member constructed of a thermoplastic resin, the mouth member sealingly bonded to a part of a periphery of the bag main body, the mouth member having a sleeve-like seal portion sealingly bonded to the bag main body, the seal portion including a first flow path and a second flow path, the first flow path opening and extending along the periphery of the bag main body, the second flow path opening at a bottom surface of the seal portion to an inside of the bag main body.

According to the liquid bag of the present invention, the mouth member includes the two flow paths, the first flow path bent in a substantially L shape in an inside of the seal portion and opening and extending along the periphery of the bag main body, the second flow path opening at the bottom surface of the seal portion to the inside of the bag main body. This structure permits partitioning of the inside of the bag main body into a section on the first flow path side and a section on the second flow path side by partially heat-welding together opposed parts of the sheet of the bag main body when the mouth member is bonded to the bag main body.

More specifically, a partitioning welded-joint may be formed by heat-welding opposed parts of the sheet of the bag main body to partition the bag main body into a first space section that communicates with the first flow path and a second space section that communicates with the second flow path. In such a case, a communication path that allows communication between the first space section and second space section may be formed in a part of the partitioning welded-joint so as to send a gas from the first flow path or second flow path via the communication path into the second flow path or first flow path. Further, the communication path may be constituted of a large number of fine paths to introduce a gas from the first flow path to the first space section or from the second flow path to the second space section for bubbling the gas in a liquid contained in the second space section or the first space section. Preferably, the first space section is formed as a guide path for a gas and/or liquid that extends along the periphery of the bag main body and the large number of fine paths are formed at a lower section of the guide path. When forming a guide path in a bag body in which a part thereof is heat-welded adjacent to a mouth member, the thickness of the mouth member makes it difficult to longitudinally form the guide path, and usually a separate pipe member is required.

According to the present invention, the guide path can be formed by heat-welding the opposed parts of the sheet at locations above and below the side opening formed in the seal portion so as to form the partitioning welded-joint along the periphery of the bag main body. Further, it is possible to form the partitioning welded-joint that extends from the mouth member along the periphery of the bag main body to the bottom thereof and further across the bottom to give the guide path that utilizes the periphery of the bag main body as its walls so as to save space in the bag main body, whereby the formation process of the guide path can be simplified. In such a case, if the large number of fine paths are formed in a part of the guide path along the bottom of the bag main body, the fine paths serve either as gas outlets of the guide path for guiding a gas into the bag main body or as liquid inlets of the guide path for guiding to the outside a liquid contained in the bag main body. When the liquid bag is used as a humidifier, for example, the above structure is advantageous in that the gas introduced can be bubbled from the bottom of the liquid bag, which permits a high contact efficiency of the gas and liquid and ensures bubbling even when there is only a small amount of liquid left in the bag main body, making good use of water (sterilized water). Also when the liquid bag is used as a nebulizer, for example, the above structure is advantageous in that water can be sucked up via the guide path to the outside until there is substantially no water left in the bag main body, making good use of water (sterilized water).

According to the present invention, the guide path of the bag main body is preferably constituted of a self-hold tunnel-shaped space formed in advance because a gas can be introduced smoothly with a reduced resistance or because a liquid can be sucked up smoothly from the bag main body without being blocked. The self-hold tunnel-shaped space is not particularly limited. The self-hold tunnel-shaped space may be formed by heating of at least one of the opposed parts of the sheet. More specifically, the self-hold tunnel-shaped space may be formed by: heating part of at least one of the opposed parts of the sheet for softening; maintaining it in a tunnel shape; and then cooling (including "naturally cooling") it for hardening. More specifically, a heated fluid (water, air or the like) may be introduced between opposed parts of the sheet (for example, a 80–300 μm thick sheet of polyethylene resin or polypropylene resin); or an unheated fluid may be introduced and then heated from the outside; or these may be combined appropriately, each of the above steps being followed by: pressing part of the bag main body other than a tunnel shaped space to be formed (i.e., pressing part that has a bag shape) to expand the intended part to a tunnel shape; maintaining the shape; and cooling for hardening to form the self-hold tunnel-shaped space. Or, the self-hold tunnel-shaped space may be formed by heating opposed parts of the sheet, reducing the pressure from the outside to expand the intended part and maintaining the shape, followed by cooling for hardening. The large number of fine paths are formed as non-welded areas by intermittently heat-welding opposed parts of the sheet of the bag main body. More specifically, the large number of fine paths may easily be formed at once by heat-pressing opposed parts of the sheet with comb-teeth shaped pins interposed between the opposed parts of the sheet and extracting the pins. Or, the fine paths may be formed by putting opposed parts of the sheet between a pair of opposed molds identical in structure each having a plurality of grooves provided in a line in correspondence with the fine paths and heat-sealing the parts of the sheet. The heat-welding is carried out so that the fine paths are formed as non-welded areas having, for example, an average width of 0.5–10.0 mm, preferably 0.5–3.0 mm with an appropriate average pitch (0.1–100.0 mm, preferably 2.0–8.0 mm).

According to the present invention, the seal portion of the mouth member is preferably shaped in a substantially rhombic prism. This shape facilitates and ensures, when the guide path is formed, heat-welding of the bag main body (opposed parts of the sheet) at a connection area between the side opening of the seal portion and the guide path. If the two flow paths of the mouth member extended straight to form their respective openings at the bottom surface of the seal portion, a longitudinal partitioning welded-joint would be required between the two flow paths to partition the bag main body. However, making the longitudinal welded-joint is difficult or impossible (as described above) because of the thickness of the mouth member. Also, although it is conceivable to form the mouth member in a shape having two rhombic prisms arranged side by side as an integral part and to heat-weld part of the bag main body to form a welded-joint that extends longitudinally from a thin-walled boundary area between the combined rhombic prisms, this results in an increase in size and complexity of shape of the mouth member, which also increases difficulties and costs in manufacturing. As compared to this, the present invention, which may be constructed so that the first flow path is formed as a bent path and the side opening thereof is formed at one top of a substantially rhombic shape in cross section of the seal portion, permits heat-welding of the opposed parts of the sheet of the bag main body at locations above and below the side opening formed at the one top of a substantially rhombic shape in cross section of the seal portion. Consequently, the present invention facilitates and ensures, with a simple structure, formation of the guide path along the periphery of the bag main body without using a pipe member (oxygen-introducing pipe or the like) while saving spaces.

According to the present invention, the mouth member may further comprise a duct portion from which the seal portion extends, the duct portion having a first duct portion that communicates with the first flow path and a second duct portion that communicates with the second flow path. In such a case, the second duct portion of the duct portion in the mouth member may have a tube-connecting port connectable to an elastic tube and a pipe-connecting port connectable to a pipe for flowing a liquid and/or gas. When the liquid bag is used as a humidifier (oxygen inhaler), for example, this structure permits use of the liquid bag in such a state that one end of the pipe whose other end is connected to an outlet of an oxygen cylinder is connected to an opening of the first duct potion via a connector and that one end of the elastic tube whose other end is connected to an oxygen mask is connected to the tube-connecting port. When the liquid bag is used as a nebulizer (sprayer), the structure permits use of the liquid bag in such a state that a spray nozzle is connected to the opening of the first duct portion to which oxygen is supplied from an oxygen cylinder and that one end of a drain pipe whose other end is connected to a drain provided on the spray nozzle is connected to the pipe-connecting port.

Further, a distal end of the tube-connecting port may be sealingly welded in such a way as to allow twist-off opening, and the opening of the first duct portion and the pipe-connecting port of the second duct portion may be respectively closed with films heat-welded thereon. By doing so, a liquid contained in the liquid bag can be prevented from escaping out of the flow paths during transportation, storage or handling, and the liquid contained in the liquid bag can be cut off from outside air, permitting maintenance of sanitary conditions. For use, the films provided on the connecting opening of the first flow path and the drain pipe-connecting port of the second flow path can be pierced with ports of connecting members when these ports enters the connection opening and ports so as to allow communication, while the distal end of the tube-connecting port of the second flow path can be opened by twisting off. This eliminates the need to directly contact the connecting opening and ports by the hand to join the necessary connecting members, thereby allowing setting of a humidifier or nebulizer under hygienic conditions. This will be explained in greater detail in embodiments to be described later. However, the methods of closing the opening and ports in the duct portion are not limited to these, but for example, a method of closing them with, for example, a rubber stopper or the like may be employed.

According to the present invention, there is no limitation for the resilient thermoplastic resin sheet that constitutes the bag main body as long as it is usable for a liquid storage bag. Examples of materials of the sheet include resins such as a polyethylene resin, a polypropylene resin, a polyethylene terephthalate resin, an ethylene-vinyl alcohol copolymer (EVOH resin) and the like, and multilayer resins such as a polyethylene/nylon multilayer resin, a polyethylene/aluminum foil multilayer resin and the like, each having a thickness of 0.1–1.00 mm. Among these, preferable are resins having no permeability to gases such as an ethylene-vinyl alcohol copolymer, a polyethylene/aluminum foil multilayer resin and the like because these resins aid the prevention of oxidation of contained chemical solutions. The liquid bag of the present invention, which is constructed of the resilient thermoplastic resin sheet, is pliant as a whole and has an effect of reducing bubbling noise.

The mouth member is not particularly limited as long as it is made of a hard thermoplastic resin. Examples of materials of the mouth member include a polyethylene resin, a polypropylene resin, a polyethylene terephthalate resin, an ethylene-vinyl alcohol copolymer (EVOH resin) and the like.

Examples of gases to be bubbled by using the liquid bag of the present invention in a liquid contained in advance in the liquid bag include air, oxygen, nitrogen, carbon dioxide, a mixture of these gases and the like. Examples of liquids to be contained in advance include water, oils and the like. The "water" means various kinds of water to which a chemical substance or another liquid (e.g., alcohol) has been added (aqueous solution).

Specific examples of liquid bags include an oxygen inhaler (humidifier for adding an appropriate moisture content to oxygen) and nebulizer (sprayer) for medical or emergency use mentioned above, a device for adding a liquid component to a gas to control humidity or air, an unsophisticated bag (oxygen is bubbled) such as a goldfish basin, a bag for preventing oxidation of a chemical substance (nitrogen is bubbled), a bag for stirring soapy water (frothing up soapy water by bubbling air) and the like. The bag for preventing oxidation of a chemical substance may be used so that after oxygen bubbling, the liquid is not discharged but is stored for a long term with the bag sealed. Examples of usages of the liquid bag wherein no communication path is formed in the partitioning welded-joint that partitions the bag main body into the first space section and second space section include the usage as a liquid bag for containing a hair dye wherein a partitioning welded-joint partitions the bag main body so that a capacity of the first space section to a capacity of the second space section is at a predetermined ratio and wherein different liquids respectively contained in the first space section and second space section are ejected when used via the first flow path and second flow path to the outside to be mixed together.

According to the liquid bag of the present invention, the amount and ratio of liquids or gases to be filled can be set freely according to purposes. Especially as compared to a hard liquid bottle of larger size, the liquid bag of the present invention is advantageous in that without completely filling an empty space with contents, the liquid bag can be sealed after extracting a gas contained in the empty space, eliminating the need to pay an attention to contamination of the gas and that when an unstable substance (oxygen or the like) is contained in the liquid bag, there is no need to substitute the substance with an inert gas (nitrogen or the like). As compared again to the hard liquid bottle of larger size, the liquid bag is advantageous in that when being packed in boxes or carried on shelves, the liquid bags can be packed or stacked in various directions, reducing waste spaces and thus making effective use of spaces.

According to the liquid bag of the present invention, liquid bags of the same shape and usage contains the same amount of a liquid to be used per unit time. Therefore, varying the amount of the liquid can adjust time (for example, 30 min., one hour, two hours and the like). Further, several liquid bags may be joined together to adjust time (30 min.+one hour=one hour and 30 min.)

In another aspect, the present invention provides a mouth member for a liquid bag, the mouth member comprising: a sleeve-like seal portion to be sealingly bonded to a part of a periphery of a bag main body for containing a liquid, the seal portion including a first flow path and a second flow path, wherein the mouth member is characterized in that the first flow path opens at a side surface of the seal portion and that the second flow path opens at a bottom surface of the seal portion. Because of the first flow path opening at the side surface of the seal portion, the guide path (described above) can be formed simultaneously with the welding of the bag main body and mouth member.

In still another aspect, the present invention provides a method of producing a mouth member for a liquid bag by injection-molding, the mouth member comprising: a sleeve-like seal portion sealingly bonded to a part of a periphery of a bag main body for containing a liquid, a duct portion from which the seal portion extends, and a flow path bent in the duct portion, the method being characterized by comprising: integrally forming, by injection-molding, a thin-walled weak cylindrical portion joined to a distal opening of the duct portion, a cylindrical body portion joined to a distal end of the weak portion, and a redundant portion provided adjacent to a distal opening of the body portion; and melting the redundant portion with heat, after the injection molding, to hermetically seal the distal opening of the body portion with the molten redundant portion so that the distal opening of the duct portion is closed in a manner capable of being opened by applying a force.

More specifically, the mouth member for the liquid bag comprises a seal portion and a duct portion, the duct portion having a flow path which is bent therein and a distal opening which is closed in a manner capable of being opened by applying a force. The mouth member is produced as follows. Inner molds that serve as cores are inserted into sections of a mold of a injection-molding machine via portions of the mold that correspond to the opening on the seal portion side and the opening of the duct portion side, respectively. Then, a resin is injected and allowed to solidify so as to facilitate integral formation of: the thin-walled weak cylindrical portion joined to the distal opening on the duct portion; the cylindrical body portion joined to the distal end of the weak portion; and the redundant portion provided adjacent to the distal opening of the body portion. After this, the redundant portion is melted by using a heated plate, a soldering iron or the like, and the distal opening in the body portion can easily be hermetically sealed with the molten redundant portion. Thus, as compared to a production method comprising separately producing "a separate member capable of being opened by applying a force" and welding the separate member on the distal opening on the duct portion of the mouth member, thereby closing the distal opening, the present invention, which utilizes integral formation, is advantageous in that it can provide the mouth member for the liquid bag with good quality and high efficiency at low costs.

BEST MODE FOR CARRYING OUT THE INVENTION

Figure 1:
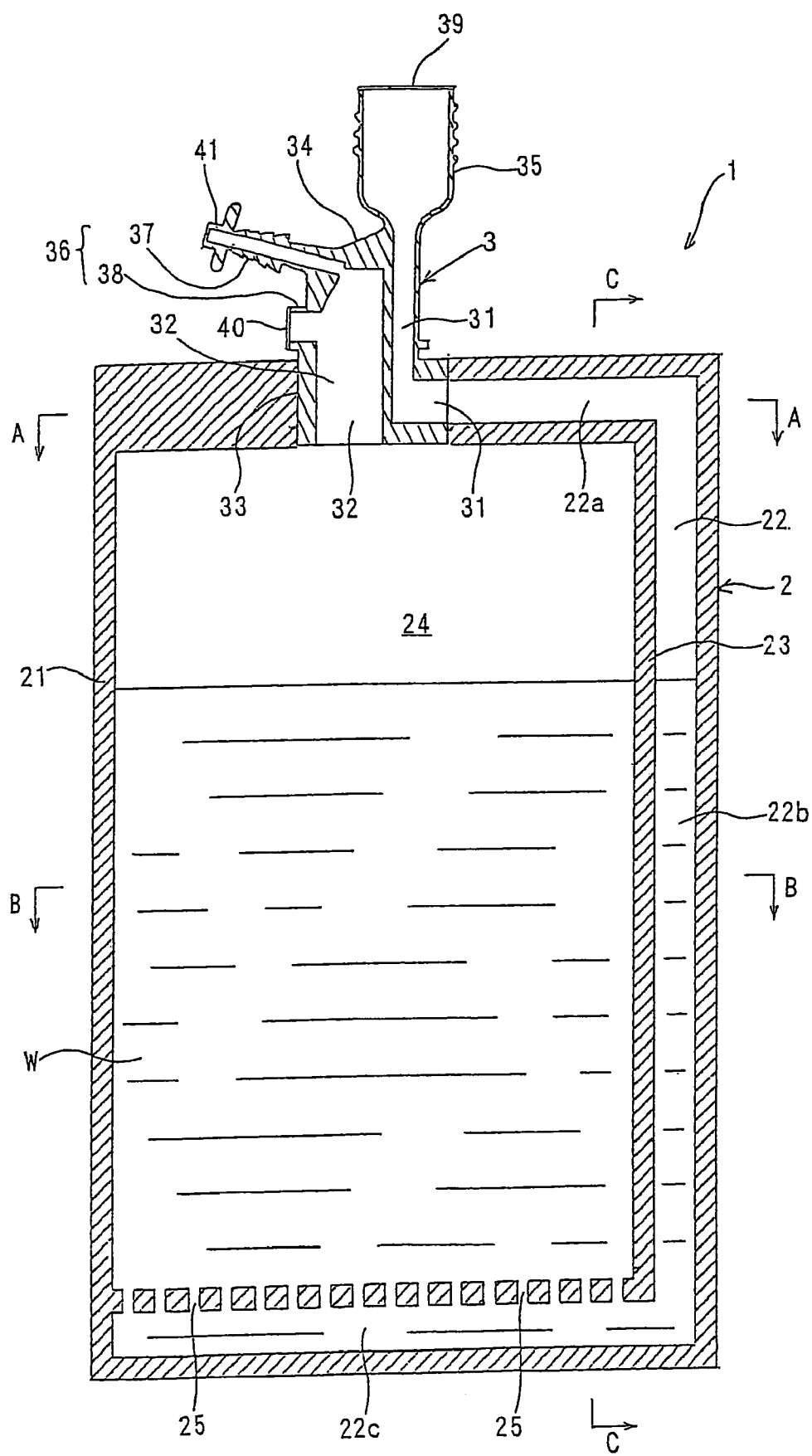
FIG. 1 is a longitudinal cross section of a liquid bag according to Embodiment 1 of the present invention.

The present invention will now be explained in detail based on the preferred embodiments shown in the drawings. It should be understood that the present invention is not limited to the embodiments.

Embodiment 1

Figure 2:
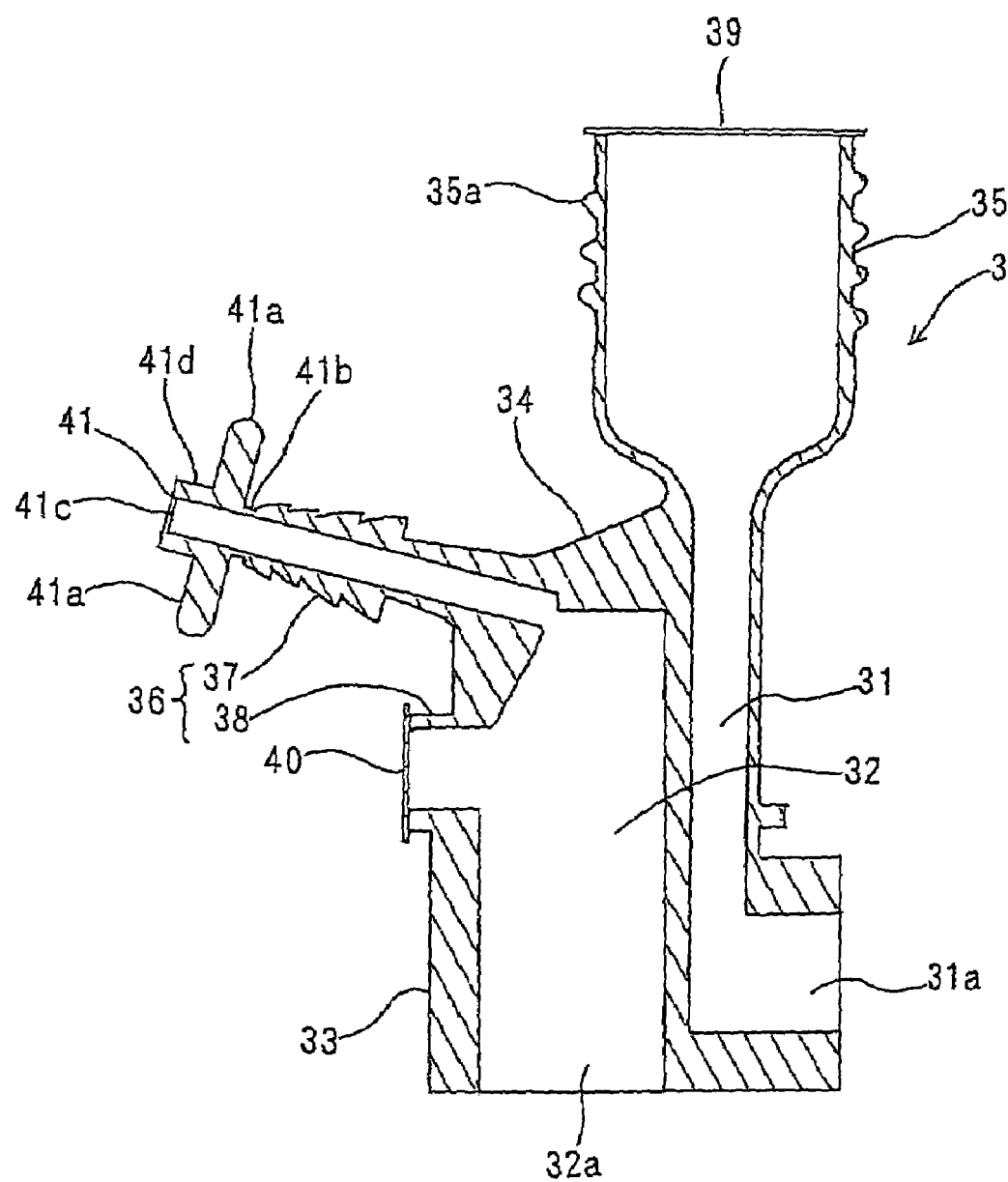
FIG. 2 is a longitudinal cross section of a mouth member according to Embodiment 1.
Figure 3:
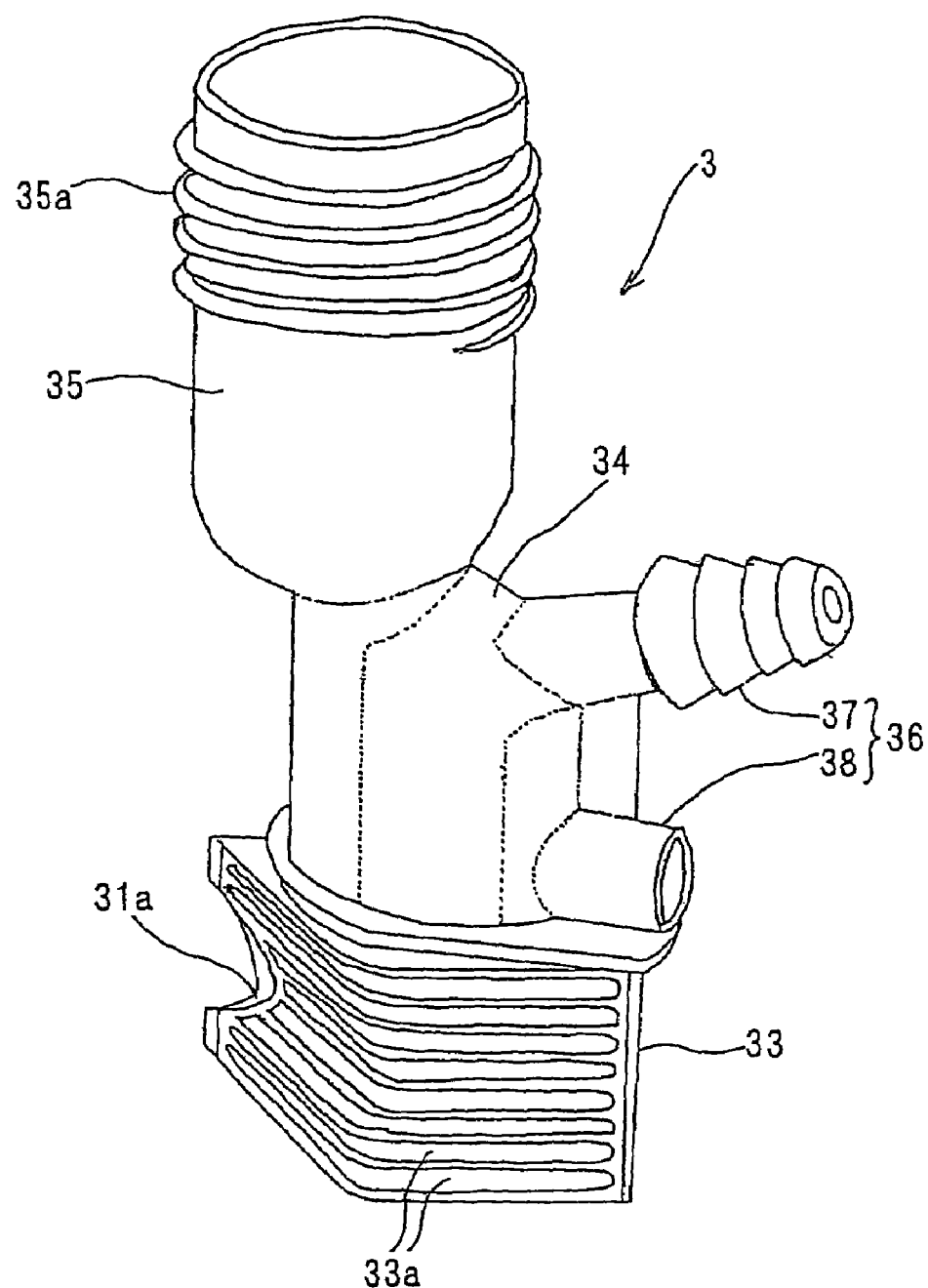
FIG. 3 is a perspective diagram of a mouth member according to Embodiment 1 in a state that an opening and ports of the mouth member are opened.
Figure 4:
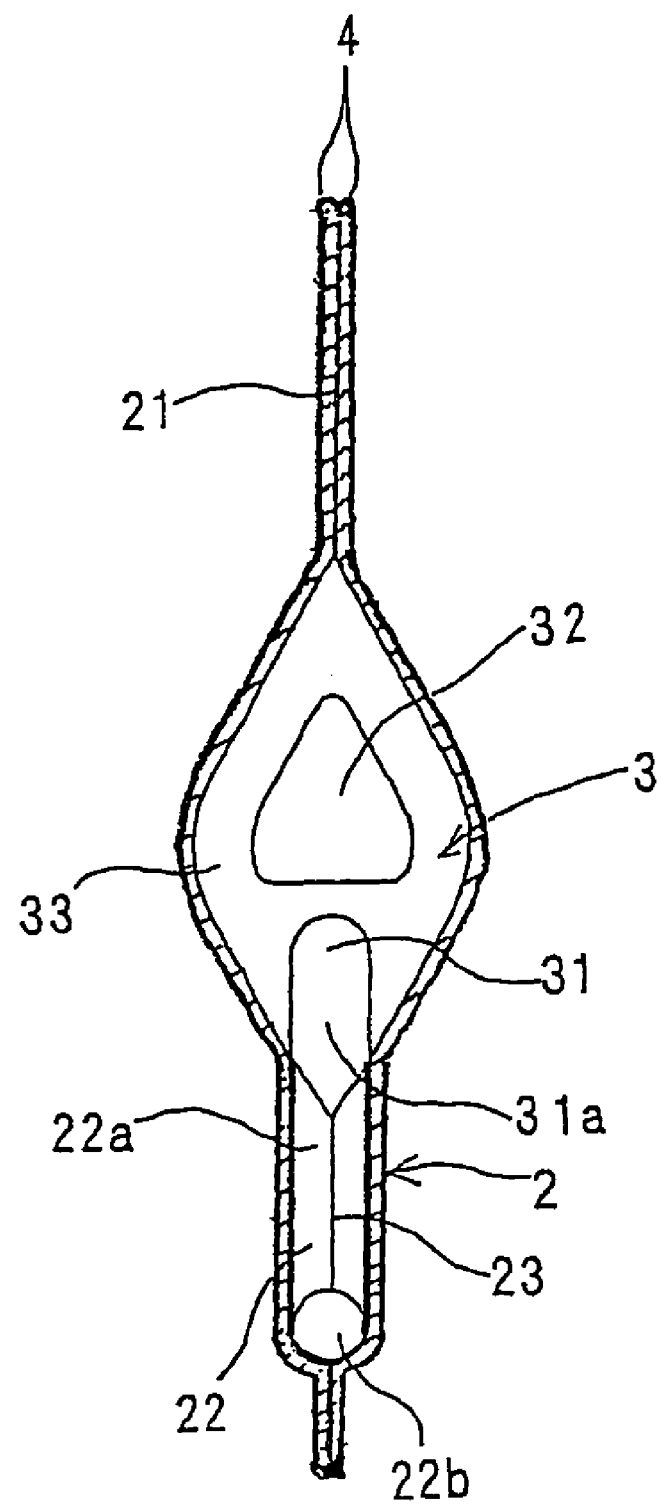
FIG. 4 is a cross section taken on line A—A of FIG. 1.
Figure 5:
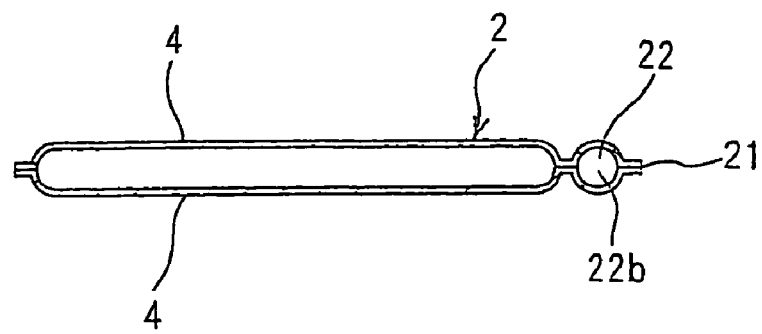
FIG. 5 is a cross section taken on line B—B of FIG. 1.
Figure 6:
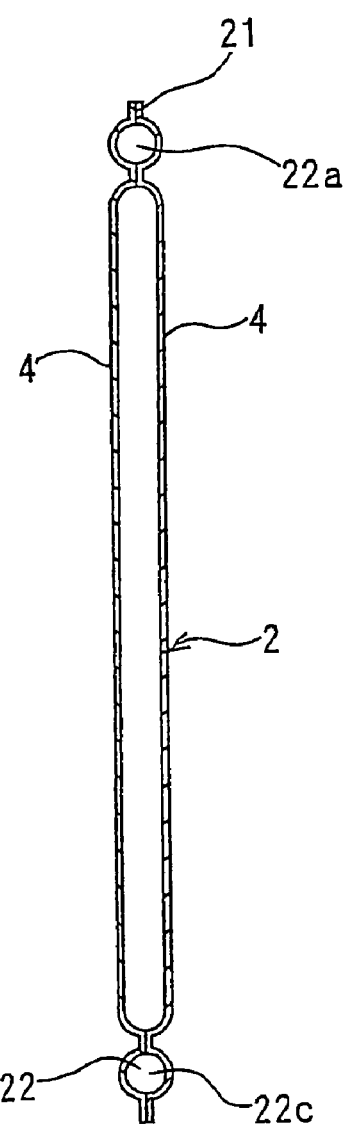
FIG. 6 is a cross section taken on line C—C of FIG. 1.
Figure 7:
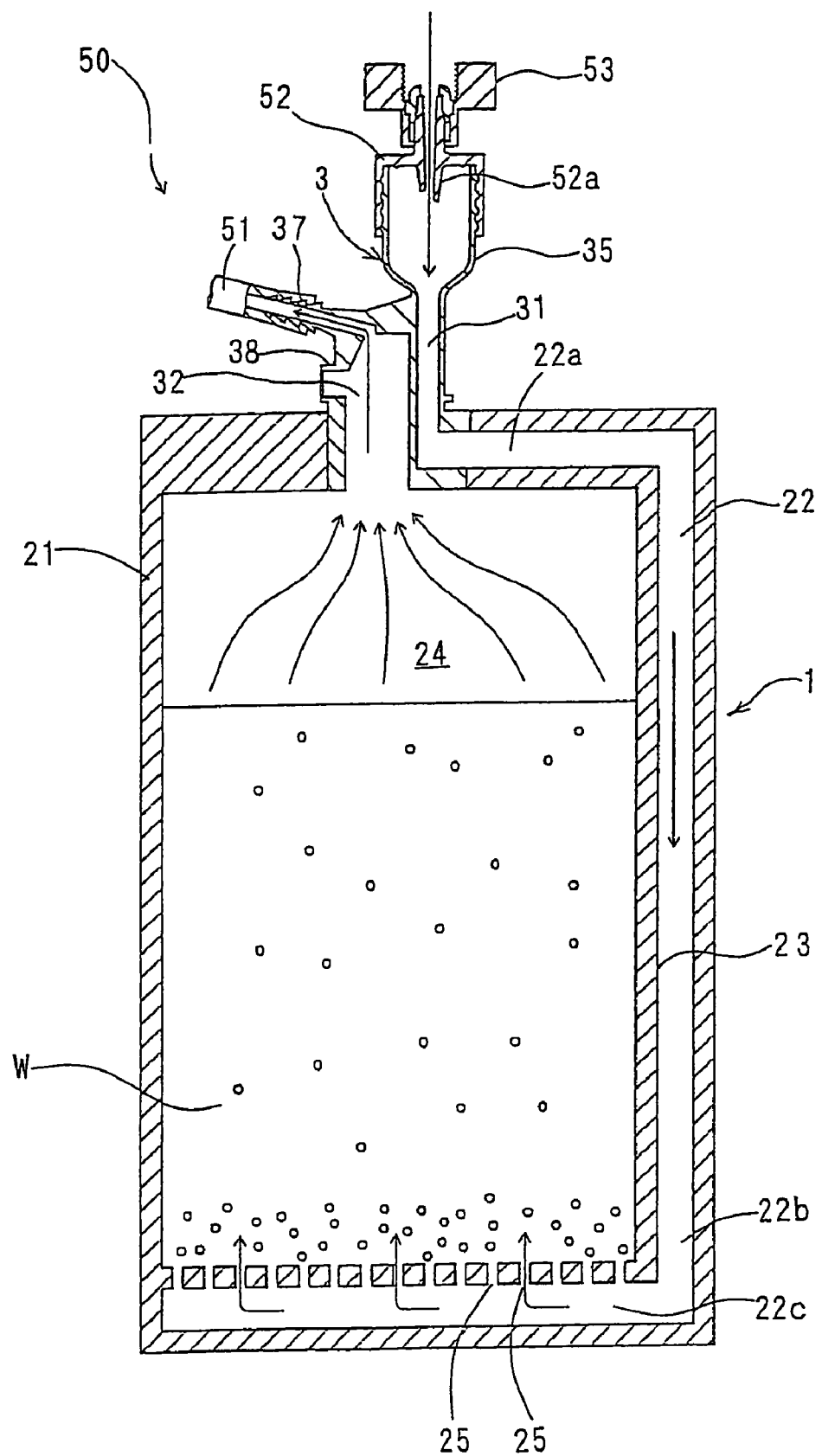
FIG. 7 is a longitudinal cross section showing a use embodiment of the liquid bag as a humidifier.
Figure 8:
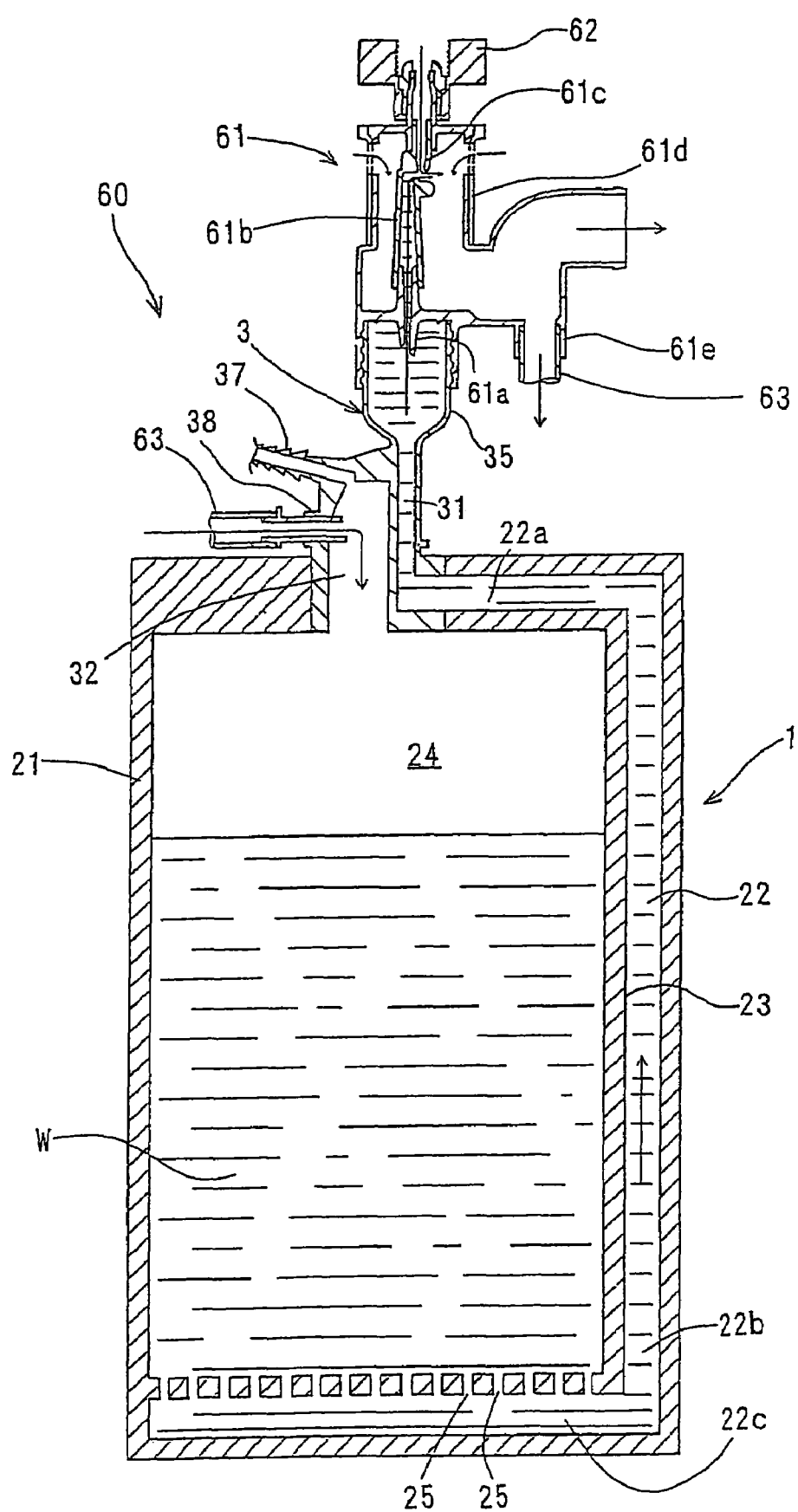
FIG. 8 is a longitudinal cross section showing a use embodiment of the liquid bag as a nebulizer.

FIG. 1 is a longitudinal cross section of a liquid bag according to Embodiment 1 of the present invention; FIG. 2 is a longitudinal cross section of a mouth member according to Embodiment 1; FIG. 3 is a perspective diagram of a mouth member according to Embodiment 1 in a state that an opening and ports of the mouth member are opened; FIG. 4 is a cross section taken on line A—A of FIG. 1; FIG. 5 is a cross section taken on line B—B of FIG. 1; FIG. 6 is a cross section taken on line C—C of FIG. 1; FIG. 7 is a longitudinal cross section showing a use embodiment of the liquid bag as a humidifier; and FIG. 8 is a longitudinal cross section showing a use embodiment of the liquid bag as a nebulizer.

A liquid bag 1 mainly comprises: a bag main body 2 substantially like an envelop; water (sterilized, purified water) W contained in advance in the main bag body 2; and a mouth member 3 sealingly bonded to a part of a periphery of the bag main body 2.

The bag main body 2 is constructed of flexible thermoplastic resin sheets 4, 4 (for example, about 0.25 mm thick polyethylene resin sheets) and the bag main body 2 is shaped substantially like an envelop. Reference numeral 21 represents a peripheral welded-joint of the bag main body 2 along which the two sheets 4,4 are heat-welded by heat-pressing so as to be sealed together.

The mouth member 3 is injection-molded in one piece and has: a sleeve-like seal portion 33 sealingly bonded to the part of the periphery of the bag main body 2; and a duct portion 34 from which the seal portion 33 extends.

The seal portion 33 is shaped in a substantially rhombic prism. The seal portion 33 has, in an outer or seal surface thereof, a plurality of grooves 33a formed substantially parallel to the periphery of the bag main body 2, that is, an upper edge of the bag main body 2 to which the seal portion 33 is sealingly bonded. Forming the plurality of grooves 33a in the seal portion 33 shortens a welding time spent at the periphery to heat-weld together the opposed sheets 4, 4 of the bag main body 2 in such a manner that the seal portion 33 of the mouth member 3 is interposed at the peripheral edge. The sheets 4, 4 are heat-welded together at the circumference of a side opening 31a of the seal portion 33 to be mentioned later.

The duct portion 34 is constructed to be connectable to a humidifier or nebulizer. The duct portion 34 has: a first duct portion 35 connectable either to an outlet of a supply source (for example, an oxygen cylinder) of a gas to be introduced into the bag main body 2 or to a spray nozzle for spraying a liquid contained in the bag main body 2; a second duct portion 36 connectable either to a container that is to contain a gas to which a liquid component has been added or to a drain of the spray nozzle; and a first flow path 31 and a second flow path 32 extending from the connecting portions 35 and 36, respectively, to the inside of the bag main body 2.

The first duct portion 35 is shaped in a cup with an upward opening and has an outer periphery with screw threads 35a formed thereon, the opening closed with a film 39 heat-welded onto it.

The second duct portion 36 comprises: a tube-connecting port 37 formed obliquely upward to be connected to an elastic tube for sending from the bag main body 2 to the unillustrated container a gas to which a liquid component has been added by being introduced into the bag main body 2; and a pipe-connecting port 38 horizontally projecting to be connected to a drain pipe 63 for refluxing from a drain 52 to the bag main body 2 part of the water W after the water W is sprayed from a spray nozzle 61 (see: FIG. 8) connected to the opening of the first duct portion 35. The pipe-connecting port 38 is closed with a film 40 heat-welded onto it. The tube-connecting port 37, on the other hand, is closed at one distal end with an integrally formed cylindrical blocking portion 41, the blocking portion 41 having a closed end. There will be described in detail later a method of producing the mouth member 3 including the blocking portion 41.

The first flow path 31, which communicates with the opening of the first duct portion 35, is bent in an L shape in the inside of the seal portion 33 to reach a side opening 31a opening in a peripheral direction (a direction along the upper side) of the bag main body 2, the side opening 31a being formed at one edge of a substantially rhombic shape in cross section of the seal portion 33 and being bounded around its circumference by the seal surfaces.

The second duct portion 36 has a lower opening 32a located at a bottom surface of the seal portion 33 to the inside of the bag main body 2. The second flow path 32 extends upward from the lower opening 32a into the duct portion to be bent at a substantially right angle and thereby to communicate with the pipe-connecting port 38. A branch extends from the right-angled bend and then is bent at a predetermined upper location to extend obliquely upward, communicating with the tube-connecting port 37.

The mouth member 3 thus constructed is injection-molded in one piece. For bending and producing the first flow path 31, inner molds that serve as cores are set in sections of an injection-molding mold that correspond to sections on the first duct portion 35 opening side and side opening 31a side, respectively. For bending and producing the second mouth portion 32, fillings that serve as cores are set in sections of the injection-molding mold that correspond to the tube-connecting port 37 side, pipe-connecting port 38 side and lower opening 32a side, respectively. A molten resin is injected into the mold and allowed to solidify, thereby forming the mouth member 3. The mouth member 3 immediately after the injection-molding is in such a state that the distal end of the blocking portion 41 (see: FIG. 2) joined to the distal end of the tube-connecting port 37 is open. The distal opening is closed after the injection-molding. More specifically, the blocking portion 41 has a pair of projections 41a, 41a formed in an opposed relation at 180° on a periphery surface of a body portion 41b of the blocking portion 41, and the blocking portion 41 has a thin-walled weak cylindrical portion 41b formed in an area thereof to which is connected the distal end of the tube-connecting port 37. At the distal end of the blocking portion 41, there is provided a lid 41c that closes the tube-connecting port 37. The blocking portion 41 is formed as follows: In the injection-molding of the mouth member 3, there are integrally formed: the weak portion 41b joined to the distal end of the tube-connecting port 37; the body portion 41b joined to the distal end of the weak portion 41b; the pair of projections 41a, 41a formed on the body portion 41d; and an unillustrated redundant portion provided adjacent to the distal opening in the body portion 41d, and after the injection-molding, the redundant portion is melted with heat (for example, by pressing the redundant portion on a heated plate, a soldering iron or the like) so that the distal opening in the body portion 41d is hermetically sealed with the molten redundant portion (molten resin), thereby forming the lid 41c. Thus, the distal opening of the tube-connecting port 37 (see: FIG. 3) is closed with the blocking portion 41 in such a way as to allow twist-off opening. The pair of projections 41a, 41a, however, may be omitted from the blocking portion 41, and in such a case, the distal opening may be opened by applying on the body portion 41d a downward force in a direction to fall down the liquid bag 1 and thereby snapping the weak portion 41b.

The mouth member 3 of the liquid bag 1 before use is in such a sate that, as described above (see: FIGS. 1 and 2), the opening (connecting port) of the fist duct 35 is closed with the film 39 heat-welded onto it; the tube-connecting port 37 is closed with the blocking portion 41; and the pipe-connecting port 38 is closed with the film 40 heat-welded onto it, thereby preventing the water W from escaping out of the mouth member 3 during transportation, storage or handling and cutting off the water W contained in the bag main body 2 from outside air, preventing unwanted bacterial mingling and permitting maintenance of sanitary conditions.

The bag main body 2 further comprises a guide path 22 formed as a first space section of a substantially open-rectangular configuration by heat-welding the two opposed sheets 4, 4 by heat-pressing. That is, the bag main body 2 has a partitioning welded-joint 23 of a substantially open-rectangular configuration formed along the upper edge, one side edge (in this case, a right side edge) and a bottom edge of the bag main body 2 and distant by predetermined lengths from these edges, and thus the bag main body 2 has the guide path 22 defined by the partitioning welded-joint 23 and periphery welded-joint 21, the guide path 22 being separated from a liquid containing portion 24 that serves as a second space section.

The guide path 22 includes: an upper horizontal path 22a that extends sideways from the side opening 31a of the first flow path 31 of the mouth member 3 along the upper edge of the bag main body 2; a descending path 22b that then is bent to extend downward along the one side edge (in this case, the right side edge) of the bag main body 2; and a lower horizontal path 22c that extends sideways from the descending path 22b along the bottom edge. Part of the partitioning welded-joint 23 opposed to the lower horizontal path 22c has a large number of fine paths 25, 25 . . . formed in a line with an equal pitch (distance between centers: about 4.0 mm), the fine paths serving as communication paths for allowing communication between the guide path 22 and the liquid containing portion 24. After the guide path 22 being defined, either hot water is introduced into the guide path 22 or unheated water is introduced into the guide path 22, then, by heating, the water and the sheets are expanded to the shape of a tunnel, and (while applying an external pressure onto parts of the sheets other than the parts intended to form a tunnel shaped space) the sheets are hardened by cooling the water and the sheets, whereby each of the upper horizontal path 22a, descending path 22b and lower horizontal path 22c is given a self-hold tunnel-shaped space (width: 8 mm, overall height: 6 mm). The large number of fine paths are formed by putting the opposed sheets between a pair of opposed molds identical in structure each having a plurality of grooves provided in a line in correspondence with the fine paths and heat-sealing the sheets. After the formation of the fine paths, heat-pressing is carried out for the bottom edge.

Use Embodiment 1

Next, there will be given an example of a procedure in using the liquid bag 1 with the above construction as a humidifier.

First, with fingers placed on the pair of projections 41a, 41a of the blocking portion 41 illustrated in FIGS. 1 and 2, the neck portion 41b is twisted off to open the tube-connecting port 37 of the mouth member 3 (see: FIG. 3). As shown in FIG. 7, the tube-connecting port 37 is then inserted into and connected to one end of an elastic tube 51 whose other end is connected to an unillustrated oxygen mask to which oxygen is supplied. A connecting portion 52 is engaged with the first duct portion 35 of the mouth member 3 by means of the screw threads 35a provided on the first duct portion 35. At this time, a downwardly protruding portion of an oxygen introducing port 52a provided at the center of the connecting portion 52 pierces through the film 39 (see: FIG. 2), allowing communication between the oxygen introducing port 52a and the first flow path 31. Then, an end of a pipe for supplying oxygen from an unillustrated oxygen cylinder is connected via a main connecting portion 53 to the connecting portion 52. The pipe-connecting port 38 is left closed with the film 40 (see: FIG. 2).

The operation of a humidifier 50 constructed using the liquid bag 1 is as follows: First, oxygen is introduced from the unillustrated oxygen cylinder via the first mouth portion 31 of the mouth member 3, and then via the upper horizontal path 22a, descending path 22b, and lower horizontal path 22c and via the fine paths 25, 25 . . . into the liquid containing portion 24. At this time, the oxygen is divided into small parts by means of the large number of fine paths 25, 25 . . . and diffused from the bottom of the liquid containing portion 24 throughout the water to make bubbling possible. As a result, a sufficient content of moisture (water vapor or water in spray form) is efficiently added to oxygen obtained on a water surface in the liquid containing portion 24, and the oxygen is sent out as humid oxygen via the second flow path 32 of the mouth member 3 and via the elastic tube 51 into the oxygen mask. The self-hold tunnel-shaped space of the guide path 22 permits a smooth introduction of oxygen into the bag main body 2. Since the guide path 22 has the oxygen outlets (the large number of fine paths 25, 25 . . . ) arranged along the bottom of the bag main body 2, bubbling can be ensured even when the water W is reduced to the extent that it is close to the bottom of the bag main body 2, making good use of the water W. Also, since the bag main body 2 can be folded to a small size after the use of the bag main body 2 when the water W is reduced to a certain extent, the bag main body 2 is convenient to discard.

Use Embodiment 2

Next, there will be given an example of a procedure in using the liquid bag 1 with the above construction as a nebulizer (sprayer).

First, as shown in FIG. 8, the spray nozzle 61 is engaged with the first duct portion 35 of the mouth member 3 of the liquid bag 1 (liquid bag 1 in the state shown in FIG. 1) by means of the screw threads 35*a* provided on the first duct portion 35. At this time, a downwardly protruding portion of a liquid-introducing port 61*a* of the spray nozzle 61 pierces through the film 39 (see: FIG. 2), allowing communication between the liquid-introducing port 61*a* and the first flow path 31. The spray nozzle 61 comprises: a sucking portion 61*b* provided at an upper end of the liquid-introducing port 61*a;* a nozzle portion 61*c* provided above the sucking portion 61*b* for injecting oxygen; a guide portion 61*d* for guiding air to the outside together with oxygen containing water in a spray form; and a drain 61*e* for discharging droplets. The nozzle portion 61*c* of the spray nozzle 61 is connected via a connecting device 62 to an end of a pipe for supplying oxygen from the unillustrated oxygen cylinder. One end of the drain pipe 63 whose other end is connected to the drain 61*c* of the spray nozzle 61 is connected to the pipe-connecting port 38 of the mouth member 3. At this time, with an inserting device attached to the end of the drain pipe 63 to which the pipe-connecting port 38 is connected, the film 40 (see: FIG. 2) is pierced to allow communication between the drain pipe 63 and the second flow path 32.

The operation of a nebulizer (sprayer) 60 constructed using the liquid bag 1 is as follows: First, oxygen is supplied from the unillustrated oxygen cylinder to the nozzle portion 61*c* of the spray nozzle 61 and then the oxygen is issued in a jet into the inside of the spray nozzle 61. The issue of the oxygen in a jet from the nozzle portion 61*c* creates a negative pressure within the spray nozzle 61 to suck up the water W from the bag main body 2 via the mouth member 3 into the sucking portion 61*b*. The water in a spray form is jetted out from a small hole provided at the upper end of the sucking portion 61*b* and is added to oxygen. Air is induced from the outside by a stream of oxygen in the guide portion 61*d* that contains the water in a spray form, and the air is forced to jet out again to the outside together with the oxygen containing water in a spray form. The self-hold tunnel-shaped space of the guide path 22 reduces the resistance in the suction of the water W from the guide path 22 of the bag main body, allowing smooth addition of the water in a spray form to oxygen. Droplets formed on inner surfaces of the spray nozzle 61 are fluxed from the drain 61*c* via the drain pipe 63 and via the second flow path 32 of the mouth member 3 into the liquid containing portion 24 within the bag main man body 2. In the nebulizer 60, since the guide path 22 has the water inlets (the large number of fine paths 25, 25 . . . ) arranged along the bottom of the bag main body 2, the suction of the water W can be ensured until the water W is reduced to the extent that it is close to the bottom of the bag main body 2, making good use of the water W. Also, since the bag main body 2 can be folded to a small size after the use of the bag main body 2 when the water W is reduced to a certain extent, the bag main body 2 is convenient to discard.

Other Embodiments

In the embodiments given so forth, the bag main body is shaped substantially like an envelop (rectangularly shaped) and the guide path is of a substantially open-rectangular configuration. However, there is no limitation for the configuration of the guide path and the location where the fine paths are to be formed so long as they meet purposes for use. For example, the guide path may comprise only an upper horizontal path with fine paths provided in a part of the upper horizontal path. Alternatively, the guide path may be shaped in the inverted L comprising an upper horizontal path and a lower horizontal path with the fine paths provided at least in a part of the lower horizontal path. The bag main body may be of square, circular, oval or elliptic shape other than rectangular shape.

INDUSTRIAL APPLICABILITY

According to the liquid bag of the present invention, the mouth member includes the two flow paths, the first flow path being bent in a substantially L shape in an inside of the seal portion and opening and extending along the periphery of the bag main body, the second flow path opening at the bottom surface of the seal portion to the inside of the bag main body. This structure permits partitioning of the inside of the bag main body into a section on the first flow path side and a section on the second flow path side by heat-welding together opposed parts of the sheet of the bag main body when the mouth member is bonded to the bag main body. When forming a guide path in a bag body in which a part thereof is heat-welded adjacent to a mouth member, the thickness of the mouth member makes it difficult to longitudinally form the guide path, and usually a separate pipe member is required. According to the present invention, the guide path can be formed by heat-welding the opposed parts of the sheet at locations above and below the side opening formed in the seal portion so as to form the partitioning welded-joint along the periphery of the bag main body. Further, it is possible to form the partitioning welded-joint that extends from the mouth member along the periphery of the bag main body to the bottom thereof and further across the bottom to give the guide path that utilizes the periphery of the bag main body as its walls so as to save space in the bag main body, whereby the formation process of the guide path can be simplified.

The invention claimed is:

1. A mouth member for a liquid bag, the mouth member comprising: a sleeve shaped seal portion to be sealingly bonded to a part of a periphery of a bag main body for containing a liquid, the seal portion including a first flow path and a second flow path, wherein the mouth member is characterized in that the first flow path opens at a side surface of the seal portion and that the second flow path opens at a bottom surface of the seal portion.

2. The mouth member for a liquid bag as set forth in claim 1, wherein the first flow path is in a substantially L shape in an inside of the seal portion.

3. The mouth member for a liquid bag as set forth in claim 1, further comprising a duct portion from which the seal portion extends, the duct portion having a first duct portion for communicating with the first flow path and a second duct portion for communicating with the second flow path.

4. The mouth member for a liquid bag as set forth in claim 3, wherein the second duct portion has a tube-connecting port connectable to an elastic tube, the tube-connecting port having a distal end sealingly welded in such a way as to allow twist-off opening.

5. The mouth member for a liquid bag as set forth in claim 3, wherein the second duct portion has a pipe-connecting port connectable to a pipe for flowing a liquid and/or gas, and wherein an opening of the first duct portion and the pipe-connecting port of the second duct portion are respectively closed with films heat-welded thereon.

* * * * *